United States Patent [19]
Forestell et al.

[11] Patent Number: 6,019,716
[45] Date of Patent: Feb. 1, 2000

[54] CENTRIFUGE BAG-HOLDING DEVICE WITH CLAMP ASSEMBLY AND USES THEREOF

[75] Inventors: Sean Forestell, San Jose; Robert J. Tushinski; Richard J. Rigg, both of Mountain View; Yakov Bobrov, San Francisco, all of Calif.

[73] Assignee: Novartis AG, Basel, Switzerland

[21] Appl. No.: 09/114,616

[22] Filed: Jul. 13, 1998

[51] Int. Cl.[7] .................................................. B04B 5/02
[52] U.S. Cl. ............................................. 494/21; 494/37
[58] Field of Search ................................... 494/1, 17, 18, 494/20, 21, 31, 33, 37, 38, 45, 47, 60, 85; 210/781, 782

[56] References Cited

U.S. PATENT DOCUMENTS

| | | | |
|---|---|---|---|
| 3,239,136 | 3/1966 | Hein | 494/45 |
| 3,559,880 | 2/1971 | Naito et al. | 494/21 |
| 4,146,172 | 3/1979 | Cullis et al. | 494/18 |
| 4,195,766 | 4/1980 | Lamadrid et al. | 494/21 |
| 4,266,717 | 5/1981 | Jennings et al. | 494/45 |
| 4,582,606 | 4/1986 | McCarty | 494/45 |
| 4,617,009 | 10/1986 | Ohlin et al. | 494/45 |
| 4,909,949 | 3/1990 | Harmony et al. | 494/21 |
| 5,224,921 | 7/1993 | Dennehey et al. | 494/18 |

*Primary Examiner*—Charles E. Cooley
*Attorney, Agent, or Firm*—Melissa A. Shaw; Lynn Marcus-Wyner

[57] ABSTRACT

A device is provided for use in a centrifuge to separate or isolate material (such as pelleted cells, particulates, aggregates, compounds, blood components, and the like) from the liquid in which they are suspended while limiting or preventing loss of any of the resulting separated or pelleted material during further manipulations. The device can be inserted into a standard centrifugation bucket in a centrifuge and holds a flexible centrifuge bag. The device includes at least one damp assembly, which includes a partition that is maintained in an open position during centrifugation and in a closed position at unit gravity, thus isolating separated or pelleted material at the bottom of the flexible bag in the device after centrifugation and preventing the isolated material from being disturbed during liquid changes and other manipulations. The invention also encompasses a method for isolating material in a centrifuge bag following centrifugation utilizing the flexible bag-holding device described herein, as well as a flexible bag to be used with the device.

29 Claims, 4 Drawing Sheets

CENTRIFUGE BAG-HOLDING DEVICE WITH CLAMP ASSEMBLY AND USES THEREOF

FIELD OF THE INVENTION

The present invention relates to an apparatus and a method for separating or pelleting particulates from fluids by centrifugation while preventing the pelleted material from being disturbed during manipulations following centrifugation. The apparatus and method of this invention may also be utilized to separate materials such as liquids into fractions of different densities.

BACKGROUND OF THE INVENTION

A centrifugal pelleting operation is a common procedure used to separate solid particles (such as cells or portions of cells, particulates, aggregates, compounds and the like) suspended in a liquid. In a pelleting operation, a container, typically a test tube or a flexible bag, holding a liquid suspension is placed in a bucket of a centrifuge rotor and subjected to a centrifugal force field. Centrifugal force causes the solid material to separate from the liquid supernatant and to deposit in a clump, called a pellet, on the wall of the container perpendicular to the axis of rotation, typically at the base of the container. When the liquid is withdrawn from the container, the pellet may be removed or may be resuspended for further processing.

Such centrifuges are used in biological research and medicine. Often, the pelleted particles are of small quantity or are valuable. Very careful and delicate technique is required by the technician handling the pellets in order to prevent loss of particles or of a patient's cells from the pellet during further manipulations. This adds additional time to the process and requires skilled, highly trained handlers. Neither of these is always available and when available, add to the costs of the procedure.

In view of the foregoing, it is believed advantageous to provide an apparatus that facilitates the simple removal of supernatant from the container after centrifugation and also facilitates further manipulations of the pelleted particles without loss of partides. An apparatus that also would lend itself to incorporation into a closed system that limits direct handling of patent samples and facilitates the use of flexible cell bags for processing patient cells would be additionally beneficial.

SUMMARY OF THE INVENTION

The present invention relates to a device for use in a centrifuge to separate solid partides from the liquid in which they are suspended while limiting or preventing loss of any of the pelleted solid partides during further manipulations of the pellet. The device of the invention may also be used in a centrifuge to separate materials, such as liquids, into fractions of different densities (separating blood components being one example) while limiting or avoiding the intermingling of the fractions. According to the invention there is provided a device for holding a flexible bag, which device can be inserted into a standard centrifugation bucket in a centrifuge. The device includes at least one clamp assembly. The clamp assembly is maintained in an open position during centrifugation and in a closed position at unit gravity, thus isolating separated or pelleted material (such as cells, particulates, aggregates, compounds and the like) at the bottom of the flexible bag held in the device after centrifugation. Harvesting material (whether solvent or solute) is thereby facilitated. This is also particularly useful when the bag and contents will be further manipulated, such as for example during cell washing or medium exchanges. By preventing the cell pellet from being disturbed during liquid changes, associated cell losses can be at least minimized and preferably essentially eliminated.

One embodiment of the present invention, therefore, is a device for holding a flexible centrifuge bag within a centrifuge bucket, which device includes a housing; a compartment within the housing for holding the flexible bag in place; and at least one damp assembly mounted on the housing. The damp assembly includes a movable partition for dividing the compartment of the device into an upper section and a lower section when the partition is in a closed position; and an actuator contacting the partition for transferring a control force to move the partition from the closed position in the compartment to an open position. The clamp assembly preferably also includes at least one resilient member mounted to the partition and to the housing to provide a spring force for maintaining the partition in closed position when the control force is removed from the actuator.

Further according to the invention there is provided a method for isolating material (such as pelleted cells, particulates, aggregates, compounds, blood components, and the like) in a centrifuge bag following centrifugation. The method comprises a) arranging and configuring a device for holding a flexible centrifuge bag within a centrifuge bucket such that the device includes 1) a housing, 2) a compartment within the housing for holding the flexible bag in place, and 3) at least one damp assembly mounted on the housing, the clamp assembly including i) a movable partition for dividing the compartment of the device into an upper section and a lower section when the partition is in a closed position, ii) an actuator contacting the partition for transferring a control force to move the partition from the closed position in the compartment to an open position, and iii) optionally, at least one resilient member mounted to the partition and to the housing for maintaining the partition in closed position when the control force is removed from the actuator; b) placing a fluid containing the material to be isolated into the flexible centrifuge bag; c) providing a control force to the actuator to move the partition in the clamp assembly to an open position in the compartment of the device; d) directing the material to be isolated to the lower section of the flexible bag by means of centrifugation; and e) removing the control force from the actuator to move the partition to a closed position in the compartment of the device, to isolate the material in the lower section of the centrifuge bag below the partition.

Further according to the invention there is provided a flexible bag for receiving a fluid therein for separation of material (such as cells, particulates, aggregates, compounds, blood components, and the like) from the fluid and for isolation of the separated material. The flexible bag has a lower portion adapted to receive and hold the material to be isolated when the contents of the bag are separated by centrifugation. This lower portion is sized to accommodate the pelleted or separated material to be isolated. In a presently preferred embodiment, the lower portion of the bag is tapered. During separation, the material to be separated out is directed, by centrifugation, to the lower, preferably tapered, section of the bag.

The terms "a" and "an" mean "one or more" when used in this application, including the claims.

BRIEF DESCRIPTION OF THE DRAWINGS

The invention will be more fully understood from the following detailed description, taken in accord with the accompanying drawings, in which.

DETAILED DESCRIPTION AND PREFERRED EMBODIMENTS

Figure 1:
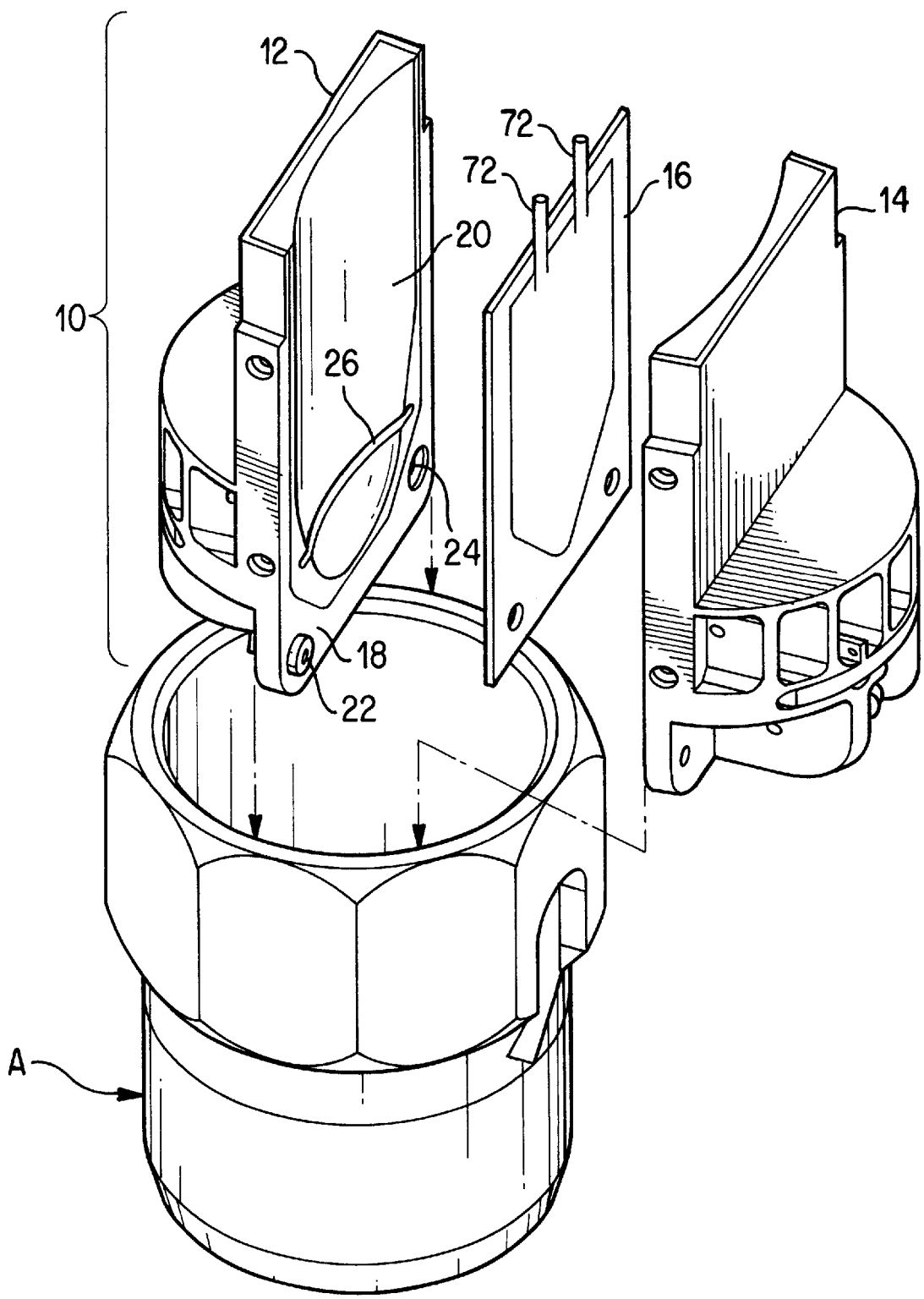
FIG. 1 is an exploded perspective view of a bag-holding device and a flexible bag according to the invention, and a centrifuge bucket (which does not form a part of the invention) in which the device holding the flexible bag is removably received.
Figure 4:
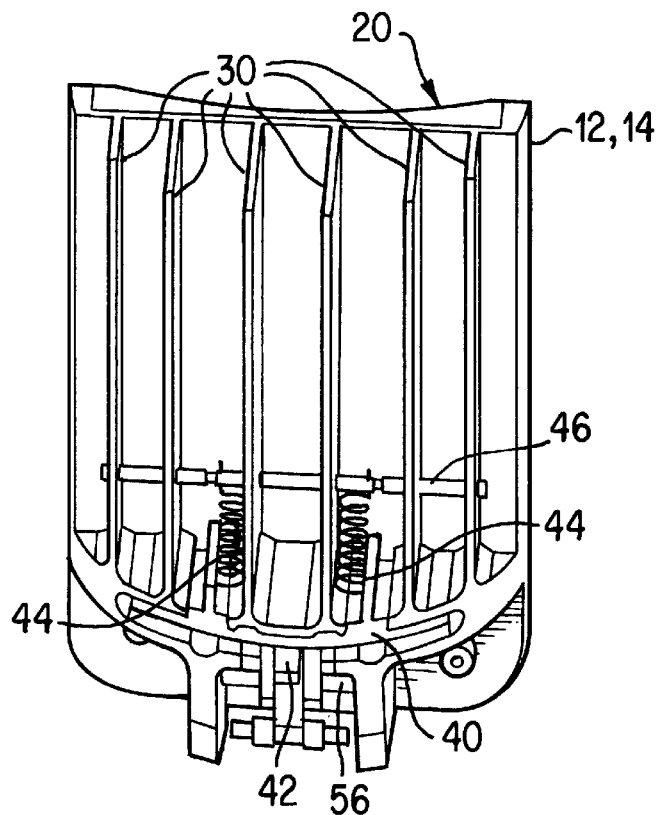
FIG. 4 is a perspective view of the outer surface of one section of the housing of the bag-holding device.

Referring to FIG. 1, flexible bag-holding device 10 is adapted for removable placement in a centrifuge bucket (the bucket designated in FIG. 1 as "A" and not forming a part of this invention). The outer shape of the body of the device is not critical and is chosen to conform to the shape of the interior of the centrifuge bucket. An alternative conformation is illustrated in FIG. 4, where vertical fins 30 are shown on the outside circumference of the device. Such fins are not a necessary requirement in the design of the device. In the example of FIG. 4, they are present to provide that the outer shape of the device corresponds to the inner shape of the centrifuge bucket while also providing for light weight with added strength. The embodiment of FIG. 1, where such fins are absent, provides an additional advantage in that the space or pocket formed between the device and the centrifuge bucket when the device is in the bucket provides a platform or chamber for additional containers. Such containers, preferably bags, may be, for example, for receipt of liquids from bag 16 during centrifugation, or they may contain components to be added to bag 16 during subsequent processing, as part of a closed system for example. Connecting tubes at ports 72 can connect such auxiliary bags to bag 16.

Device 10 has a housing formed by two sections 12, 14 that are adapted to secure a flexible bag or receptacle 16. Each of sections 12, 14 has an inner surface 18 having an inner cavity or bag bed 20. When the two sections of the housing are joined together, the inner cavities or bag beds provide a compartment for the flexible bag 16 filled with fluid, to hold the bag in place and to prevent the bag from collapsing during centrifugation. At least that portion of each of the two sections 12, 14 that includes the bag bed may be, and preferably is separable from and can be removed from the housing. In this manner, sections having bag beds of different sizes and shapes (to correspond to the sizes and shapes of different flexible bags or to the volume of suspension) may be interchangeably used in the device, allowing the device to be utilized in a variety of centrifugation procedures.

Figure 2:
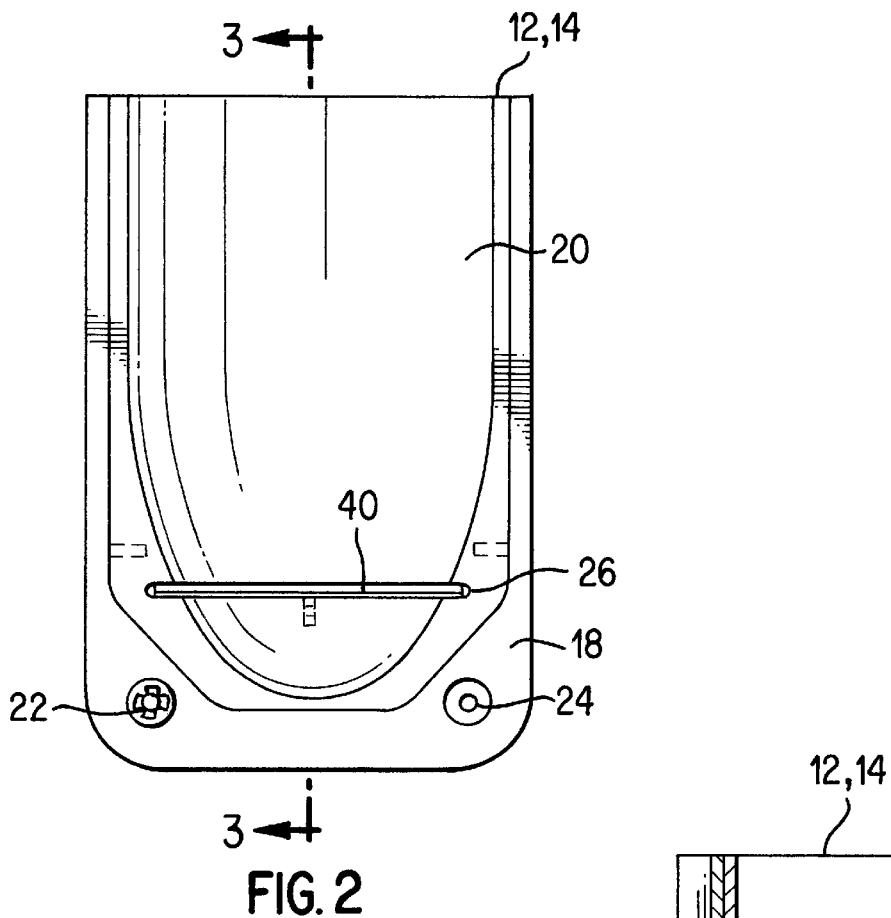
FIG. 2 is a vertical plan view of the inner surface of one section of the housing of the bag-holding device.

The two sections of the housing are held together by the inner wall of the centrifuge bucket when the device 10 is placed into the bucket. More preferably, the two sections may be held together by one or more fasteners (not illustrated), such as, but not limited to, a removable ring or band around the circumference of the device; or one or more latches, pins, screws, clamps, hinges and the like at points where the sections meet. Likewise, as illustrated in FIGS. 1 and 2, there is optionally included on the inner surface 18 of each section of the housing a protrusion 22 and a cavity 24 for mating with, respectively, a reciprocal cavity 24 and protrusion 22 on the other section. These reciprocal protrusions and cavities act as guide pins for correctly joining together and holding the two sections of the device and for alignment of the bag. The cavity and protrusion may be further modified with a hole through their centers for accommodating a pin, screw, nut and bolt, or the like, for securing the two sections together.

Figure 3:
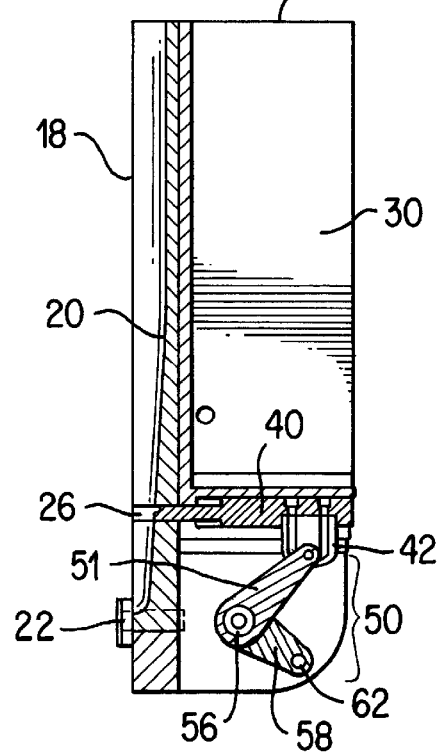
FIG. 3 shows a section through the bag-holding device along line 3—3 in FIG. 2.

Movably mounted through a slot 26 into the wall of each section 12, 14 is a partition 40, illustrated in FIGS. 2 and 3. When in the inactivated, or closed position, each partition 40 protrudes into the compartment formed by the bag bed 20, the partitions meeting in the compartment to seal off a bottom portion of the compartment and of any flexible bag positioned in the compartment. This effectively seals off and isolates the contents in the bottom portion of the flexible bag (in other words, that portion of the bag below the partition) from those contents in the portion of the bag above the partition. In the activated, or open position, as illustrated in FIG. 3, each partition 40 is retracted back from the compartment through the slot 26 to an open position, thus allowing communication and intermingling of the contents throughout the flexible bag. While in the present embodiment the partition slides perpendicularly into and out of the compartment, other ways of moving the partition are contemplated by this invention.

One or more resilient members hold partition 40 in a closed or inactivated position. In FIG. 4, the resilient member comprises two coiled springs 44, which are attached to the housing at one of their ends by means of a spring shaft 46, and to the partition 40 at their other end. Other resilient members that may be used include, but are not limited to, bar springs, rubber or elastic bands, solenoids, air cylinders, and the like as would be known to those skilled in the art. In their resting state, the resilient members provide a spring force to keep the partition in a closed position. Force (control force) against the springs is required to move the partition to an open position.

Figure 5:
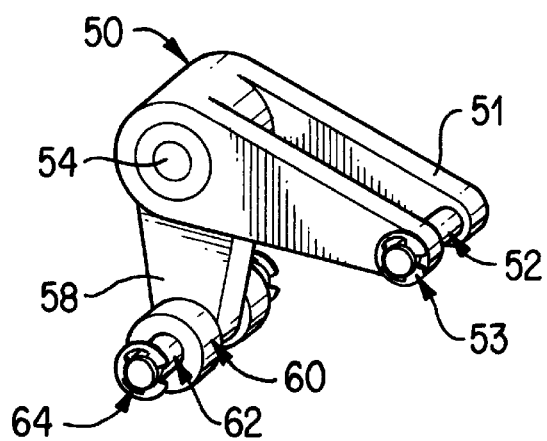
FIG. 5 is a perspective view of one embodiment of the actuator of the clamp assembly, in this example the actuator being a lever with a load acting as a gravity or centrifugal actuator.

In the practice of the present invention, in a presently preferred embodiment the opening and closing of the partition is controlled by the gravitational or centrifugal force (the control force) resulting from the rate of rotation of the centrifuge, which centrifugal force acts against the spring force of the damp assembly. A lever 50, shown in FIG. 3 as rotatably connected to the partition 40 by a driver 42, acts as a gravity or centrifugal actuator. FIG. 5 illustrates lever 50 in greater detail. Lever 50 has a partition-connecting end 51 with a drive shaft 52, for rotatable connection to the movable partition via the driver 42. Drive shaft 52 is held in place by retaining ring 53. Lever 60 also has a hole 54, for accepting a fulcrum shaft 56 (shown in FIG. 4) for mounting the lever to the housing of the device. Lever 50 has a force-receiving end 58 for transferring a control force to rotate the lever about the fulcrum shaft, which rotation of the lever will move the partition, via the partition-connecting end 51, from a closed position in the compartment of the housing to an open position. In the present embodiment, illustrated in FIG. 5, the lever actuator includes a weight or load 60 attached to force-receiving end 58. One or more weights are removably placed on a load shaft 62 and held in place by a retaining ring 64. In this manner, the load can be adjusted to meet the requirements of the particular use, such as for example the amount of gravitational force produced by the centrifuge to open the partition (the control force in this example), and the like. Alternatively, the force-receiving end 58 may be of a particular predetermined density such that it itself acts as the weight or load portion of the gravity actuator.

In operation, a force is applied to lever 50 by centrifugal force (generated when the centrifuge is spinning at a predetermined speed) acting on the load 60. The centrifugal force pulls on the load 60, which causes the lever 50 to rotate in an arc around the fulcrum shaft or pivot 56, which in turn forces down the lever end 51 that is rotatably attached to partition 40. The lever thus pulls on partition 40, as a result of which partition 40 slides to an open or activated position away from the center of the compartment and toward the circumference of the housing. As the centrifuge slows down and stops, the control (centrifugal) force on load 60 falls below the opposing spring force provided by the resilient member or springs 42. The spring force of the springs 42 causes the partition 40 to slide back to its closed position in the compartment. This isolates the material pelleted and positioned in the bottom portion of the flexible bag during centrifugation from the other materials and fluids in the upper portion of the flexible bag. The bag can now be manipulated without disturbing the isolated material below the closed partitions.

In alternative embodiments, the control force and the actuator are independent of centrifugal force. The control force can be activated manually. For example, rather than lever 50 having a load attached to force-receiving end 58, a movable bar, rod, stick, shaft, arm or the like is connected to the lever end 58 at one end (the bottom end) of the bar. The bar is positioned so that its opposite, or top, end is accessible from the top of the housing. To activate or open the partition, force is applied downward onto the bar at its top end and the bar is locked or latched into position. This downward force acts as the control force and pushes on force-receiving end 58 of lever 50 via the bar, causing the lever 50 (which functions as a manual actuator in this embodiment) to rotate in an arc around the fulcrum shaft or pivot 56, which in turn forces down partition-connecting end 51 of the lever to move partition 40 to an open or activated position. The centrifuge is then turned on. After the centrifuge has been turned off, the bar is disengaged from its locked or latched position. As the control force provided by the locked bar is released, the spring force of the resilient member or springs 42 causes the partition 40 to slide back to its closed position in the compartment.

In addition to gravity activation and manual activation, other means for transferring control force to the actuator for opening the partition may be utilized and are encompassed by this invention. For example, a solenoid (providing the control force) can be connected to the lever or other comparable actuator, such as a movable arm for example. A further means for transferring control force to activate the actuator may be a component, such as a bar or a spring, made of a "memory" metal or alloy in conjunction with a heat-exchanging device for heating the memory metal. The memory metal expands when the temperature rises, applying a control force to the actuator to move the partition to its open position, and contracts when the temperature returns to normal, removing the control force and causing the partition to return to its closed position. Other examples of providing a control force incude, but are not limited to, piezocrystals, inflatable air cushions, and the like.

The operating conditions of the present invention may be adjusted in a number of ways. For example, control of the opening and closing of the partition may be adjusted by changing the amount of control force applied to the actuator (such as, e.g., the amount of centrifugal force), or the weight or load on the actuator (in the case of gravity activation) may be varied, or the strength of the spring force of the resilient member may be adjusted. Such adaptations are within the skill in the art and would not entail undue experimentation.

The centrifuge bag holder of the invention may be used with a commercial flexible centrifuge bag, such as for example bag model 2P-0100 by AFC, Inc. Such bags normally have relatively square or flat bottoms for holding their contents. However, there is provided herein according to the present invention a new flexible centrifuge bag which works particularly well with the bag-holding device.

Figure 6:
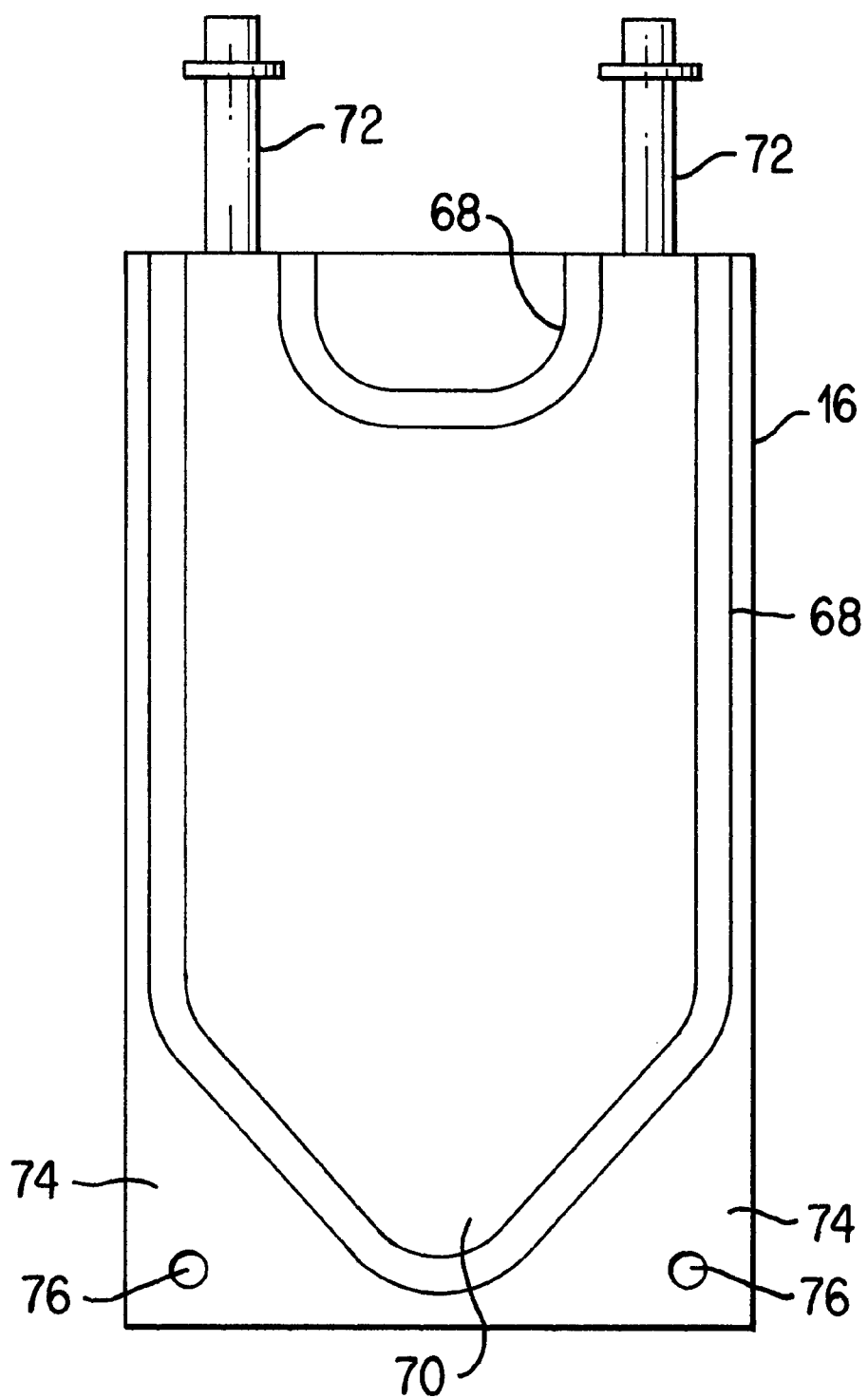
FIG. 6 is a vertical plan view of one embodiment of the flexible bag for use with the bag-holding device.

The flexible bag of the present invention, shown in more detail in FIG. 6, is preferably made from a suitable medical-grade plastic material such as polyvinyl chloride, Teflon®, polyethylene, silicon, and the like. The bag may be made according to methods known in the art, including but not limited to sealing around the edges of two plies of flexible material. In FIG. 6, the seal is indicated as heavy lines 68. The size and volume of the bag will be chosen based upon the use to which the bag will be put, such as for example the volume of fluid to be held or the type and amount of material to be separated. As illustrated in FIG. 6, bag 16 preferably has a tapered end 70 to accommodate substantially only the material to be separated out and isolated. The flexible bag may include inlet and/or outlet ports 72. The number and location of ports are not critical and will be that number or location necessary for providing adequate introduction or removal of bag contents during separation or treatment procedures.

The flexible bag of the invention is configured to fit into and be held in place by the compartment of a bag-holding device for a centrifugation bucket, as described previously herein. In the presently illustrated embodiment, bag 16 has flaps 74, which, when placed in the device, are positioned between the inner surfaces 18 of the two sections 12, 14 of the housing of the device to provide additional support for holding the flexible bag in position in the compartment of the closed device. When protrusion 22 and cavity 24 are components of the housing, holes 76 are preferably present on flaps 74 to accommodate the protrusions. While such flaps assist in positioning and holding the flexible bag in place, they are not critical to the invention and may be present or absent from the bag design.

All connections to the flexible bag can be made aseptically with a Terumo™ or other sterile connect device to provide a closed system. Such closed system is necessary, e.g., for the inoculation, transduction and culture of cells used in ex-vivo gene therapy, such as the delivery of genes to cells by recombinant retroviral vectors. The bag-holding device and flexible bag of the present invention may be used to achieve viral inoculation of cells by the procedure of spinoculation. In this process, cells (human hematopoietic stem cells being one example) are infected with viral particles at high speed centrifugation. The bag-holding device allows flexible bags to be spun at high speed without rupture of the bags, while the damp assembly feature facilitates collection of the resulting infected cells.

While there has been described what is at present considered to be the preferred embodiment of this invention, it will be clear to those skilled in the art that various alternatives, modifications, and variations may be made without departing from the invention. All the elements may furthermore be replaced with other technically equivalent elements. In the practical embodiment of the invention, the materials employed, as well as the shapes and dimensions may be any according to the requirements. It is, therefore, aimed to cover all such changes, modifications, and variations as fall within the spirit and scope of the invention.

What is claimed is:

1. A device for holding a flexible bag within a centrifuge bucket, the device comprising:
   a. a housing;
   b. a compartment within the housing for holding the flexible bag in place; and
   c. at least one clamp assembly mounted on the housing, the clamp assembly comprising:
      i. at least one movable partition for dividing the compartment into an upper section and a lower section when the partition is in a closed position;
      ii. at least one actuator contacting the partition for transferring a control force to move the partition from the closed position in the compartment to an open position when the control force is applied and to move the partition from the open position to the closed position when the control force is removed; and
      iii. at least one resilient member mounted to the partition and to the housing for maintaining the partition in the closed position when the control force is removed from the actuator.

2. A device according to claim 1 wherein the control force is centrifugal force.

3. A device according to claim 2 wherein the actuator is a lever with a load.

4. A device according to claim 1 wherein the resilient member is at least one coiled spring or at least one bar spring.

5. A device according to claim 1 wherein at least a portion of the housing comprises a bag bed, and said bag bed portion is separable from the housing.

6. A device according to claim 1 wherein the resilient member is at least one spring, the actuator is a lever with a load, and the control force is centrifugal force.

7. A method for isolating material in a centrifuge bag following centrifugation, the method comprising:
   a) arranging and configuring a device for holding a flexible centrifuge bag within a centrifuge bucket such that the device comprises:
      1) a housing,
      2) a compartment within the housing for holding the flexible bag in place, and
      3) at least one clamp assembly mounted on the housing, the clamp assembly comprising:
         i) at least one movable partition for dividing the compartment of the device into an upper section and a lower section when the partition is in a closed position,
         ii) at least one actuator contacting the partition for transferring a control force to move the partition from the closed position in the compartment to an open position when the control force is applied and to move the partition from the open position to the closed position when the control force is removed, and
         iii) at least one resilient member mounted to the partition and to the housing for maintaining the partition in the closed position when the control force is removed from the actuator;
   b) placing fluid containing the material to be isolated into the flexible centrifuge bag;
   c) providing a control force to the actuator to move the partition in the clamp assembly to an open position in the compartment of the device;
   d) directing the material to be isolated to the lower section of the flexible bag by centrifugation; and
   e) removing the control force from the actuator to move the partition to a closed position in the compartment of the device, to isolate the material in the lower section of the centrifuge bag below the partition.

8. A method according to claim 7 wherein the control force is centrifugal force.

9. A method according to claim 8 wherein the actuator is a lever with a load.

10. A method according to claim 7 wherein the resilient member is at least one coiled spring or at least one bar spring.

11. A method according to claim 7 wherein the material to be isolated comprises cells.

12. A method according to claim 7 wherein at least a portion of the housing comprises a bag bed, and said bag bed portion is separable from the housing.

13. A method according to claim 7 wherein the resilient member is at least one spring, the actuator is a lever with a load, and the control force is centrifugal force.

14. A device for holding a flexible bag within a centrifuge bucket, the device comprising:
   a. a housing comprising two sections;
   b. a compartment within the housing for holding the flexible bag in place; and
   c. a clamp assembly mounted on each section of the housing, each clamp assembly comprising:
      i. at least one movable partition for dividing the compartment into an upper section and a lower section when the partition is in a closed position;
      ii. at least one actuator contacting the partition for transferring a control force to move the partition from the closed position in the compartment to an open position when the control force is applied to the actuator; and
      iii. at least one resilient member mounted to the partition and to the housing for maintaining the partition in the closed position when the control force is removed from the actuator.

15. A device according to claim 14 wherein the resilient member is a coiled spring or a bar spring.

16. A device according to claim 14 wherein the control force is centrifugal force.

17. A device according to claim 16 wherein the actuator is a lever with a load.

18. A device according to claim 14 wherein at least a portion of each section of the housing, comprising a bag bed, is separable from the housing.

19. A device according to claim 14 wherein the resilient member is at least one spring; the actuator is a lever with a load; and the control force is centrifugal force.

20. A device according to claim 19 wherein at least a portion of each section of the housing, comprising a bag bed, is separable from the housing.

21. A method for isolating material in a centrifuge bag following centrifugation, the method comprising:
   a) arranging and configuring a device for holding a flexible centrifuge bag within a centrifuge bucket such that the device comprises:
      1) a housing comprising two sections,
      2) a compartment within the housing for holding the flexible bag in place, and
      3) a clamp assembly mounted on each section of the housing, each clamp assembly comprising:
         i) at least one movable partition for dividing the compartment of the device into an upper section and a lower section when the partition is in a closed position, ii) at least one actuator contacting the partition for transferring a control force to move the partition from the closed position in the compartment to an open position when the control force is applied to the actuator, and iii) at least one resilient member mounted to the partition and to the housing for maintaining the partition in the closed position when the control force is removed from the actuator;

b) placing fluid containing the material to be isolated into the flexible centrifuge bag;

c) providing a control force to the actuators to move the partitions in the clamp assemblies to an open position in the compartment of the device;

d) directing the material to be isolated to the lower section of the flexible bag by centrifugation; and e) removing the control force from the actuators to move the partitions to a closed position in the compartment of the device, to isolate the material in the lower section of the centrifuge bag below the partitions.

22. A method according to claim 21 wherein the control force is centrifugal force.

23. A method according to claim 22 wherein the actuator is a lever with a load.

24. A method according to claim 21 wherein at least a portion of each section, comprising a bag bed, is separable from the housing.

25. A method according to claim 21 wherein the resilient member is at least one coiled spring or at least one bar spring.

26. A method according to claim 21 wherein the resilient member is at least one spring; the actuator is a lever with a load; and the control force is centrifugal force.

27. A method according to claim 26 wherein at least a portion of each section of the housing, comprising a bag bed, is separable from the housing.

28. A method according to claim 26 wherein the material to be isolated comprises cells.

29. A method according to claim 21 wherein the material to be isolated comprises cells.

* * * * *